United States Patent
Székely et al.

[11] Patent Number: 5,192,793
[45] Date of Patent: Mar. 9, 1993

[54] PLANT PROTECTIVE MICROEMULSION COMPOSITION COMPRISING PYRETHROIDS

[75] Inventors: István Székely, Dunakeszi; András Szegö; Laszio Pap, both of Budapest; Lajos Nagy, Szentendre; Viktória Kollárik née Hasek, Budapest; Katalin Mármarosi née Kellner, Biatorbágy; Zoltán Karádi, Budapest; Andrea Tóth, Solymár; György Szucsány, Budapest, all of Hungary

[73] Assignee: Chinoin Gyogyszer es Vegyeszeti Termekek Rt., Budapest, Hungary

[21] Appl. No.: 548,917

[22] PCT Filed: Dec. 21, 1989

[86] PCT No.: PCT/HU89/00065
§ 371 Date: Jul. 24, 1990
§ 102(e) Date: Jul. 24, 1990

[87] PCT Pub. No.: WO90/06681
PCT Pub. Date: Jun. 28, 1990

[30] Foreign Application Priority Data
Dec. 22, 1988 [HU] Hungary ............... 6558/88

[51] Int. Cl.⁵ ............... A01N 37/34; A01N 43/38; A01N 53/00; A01N 31/14
[52] U.S. Cl. ............... 514/421; 514/521; 514/531
[58] Field of Search ........ 514/68, 521, 143, 421, 514/531

[56] References Cited

U.S. PATENT DOCUMENTS

| | | | |
|---|---|---|---|
| 4,902,510 | 2/1990 | Garden | 514/68 |
| 4,997,642 | 3/1991 | Curtis et al. | 514/521 |
| 5,013,754 | 5/1991 | Hidasi et al. | 514/521 |

OTHER PUBLICATIONS

Hackh's Chemical Dictionary, p. 313, Grant (1986).
CIPAC Handbook, vol. 1, Analysis of Technical and Formulated Pesticides, Ashworth et al (1976), pp. 875–879.

*Primary Examiner*—Richard L. Raymond
*Assistant Examiner*—S. Mark Clardy
*Attorney, Agent, or Firm*—Herbert Dubno; Jonathan Myers

[57] ABSTRACT

A solution of a plant protective agent is disclosed, which comprises per liter of solution
1 to 150 g/l of one or more synthetic pyrethroid(s) as active ingredient(s) and
40 to 70 g/l of ethoxylated (EO=10 to 14)-propoxylated (PO)=18 to 22) nonylphenol,
10 to 20 g/l of linear calcium dodecylbenzenesulfonate,
90 to 120 g/l of polyoxyethylene(20)-sorbitan monolaurate as the surface active agents, and a solvent mixture (A) consisting of
9 to 11% by volume of hydrogenated aliphatic hydrocarbon containing 45% of naphthene, 18 to 30% by volume of propylene glycol, 28 to 35% by volume of pine fatty acid, 23 to 30% by volume of sunflower oil, 5 to 10% by volume of an 1:1 by volume mixture of methanol or ethanol with isobutanol in an amount to complete the volume to 1 liter.

5 Claims, No Drawings

PLANT PROTECTIVE MICROEMULSION COMPOSITION COMPRISING PYRETHROIDS

FIELD OF THE INVENTION

This invention relates to novel plant protective microemulsion compositions, more particularly to solutions containing pyrethroids as active ingredients as well as to stable aqueous microemulsions prepared therefrom. The invention further relates to the preparation and use of these solutions and microemulsions.

BACKGROUND OF THE INVENTION

The aqueous microemulsions according to the invention can be transformed to other compositions such as aerosols by using suitable auxiliary materials.

It is known that synthetic pyrethroids are used to a continuously increasing extent in the state of the art plant protection since a satisfactory protection can be achieved by applying the active ingredient in amounts as low as 10 to 100 g/ha and on the other hand, the residue of the active ingredient becomes negligible within a relatively short time of decomposition. The pyrethroid-type active ingredients are used in the form of wettable powders (WP), suspension concentrates (FW) and most frequently as microemulsion compositions (EC). General demands made on the state of the art emulsion concentrates comprise a) ensuring the very dilute emulsion phase state in the concentration for application by an economical amount [75 to 150 g/liter (abbreviated: g/l] of a surface active agent; and b) avoiding the use of xylene as solvent because of problems connected with safety, environmental protection and phytotoxicity.

The low amount of the surface active agent can be ensured by a suitable selection of state of the art surface active substances. For replacing xylene, the solvent manufacturers developed specific but expensive novel types of solvents whereas the formulating manufacturers made efforts to replace the solvents by aqueous systems. Thus, in the German patent specification NO. 3,235,612, aqueous microemulsions are described which contain: 0.1 to 80% by weight of active ingredient together with 1 to 20% by weight of a particular emulsifier mixture and optionally 1 to 30% by weight of organic solvent, being partly miscible with water; as well as water. The particular emulsifier is a mixture of an alkylaryl polyglycol ether with an alkylarylsulfonate salt. The emulsion stability of the emulsion concentrates reported in the German patent specification No. 3,508,643 is ensured by polyvinyl alcohol and an organic acid. The aqueous microemulsions described in the German patent specification No. 3,624,910 contain as emulsifiers a phenol or a phenolate salt substituted by ethoxylated and phosphorylated styryl group in combination with one or more non-phosphorylated emulsifying agent(s) together with 5 to 30% by weight of an usual solvent.

The aqueous microemulsions set forth in the published European patent application No. 0,160,182 contain pyrethroids and phosphoric acid esters as active ingredients and ethoxylated tristyrylphenol, ethoxylated distyrylphenol-ammonium sulfate and an alkylarylsulfonate as emulsifying agents. Emulsion concentrates containing low molecular aliphatic alcohols and ketones as stabilizing agents are described in the published Japanese patent application No. 51-59778.

Another problem of the EC-type compositions arises in that a stable spray liquid, required to remain stable in most cases for at least 24 hours, has to be prepared from the given emulsion concentrates by using waters with various hardnesses. In addition, synthetic pyrethroids are weakly soluble in aliphatic hydrocarbons and apolar solvents which in turn are preferred from the viewpoint of phytotoxicity, environmental protection and safety; thus, they can meet the criterion of the cold-resistance only with difficulties.

OBJECT OF THE INVENTION

The object of the invention is to prepare an emulsion solution (pre-formulation) with a composition meeting the demands made on the state of the art emulsion concentrates such as the low surface active agent content, absence of aromatic solvents and the possibility of preparing a stable aqueous microemulsion even under the extreme use conditions.

SUMMARY OF THE INVENTION

Thus, the present invention relates to a novel solution of a plant protective agent, 1 liter of which contains 1 to 150 g/l of one or more synthetic pyrethroid(s) as active ingredient(s) and 40 to 70 g/l of ethoxylated (EO=10 to 14)-propoxylated (PO=18 to 22) nonylphenol, 10 to 20 g/l of linear calcium dodecylbenzenesulfonate, 90 to 120 g/l of polyoxyethylene(20)-sorbitan monolaurate as surface active agents, and a solvent mixture (A) consisting of 9 to 11% by volume of hydrogenated aliphatic hydrocarbon containing 45% of naphthene, 18 to 30% by volume of propylene glycol, 28 to 35% by volume of pine fatty acid, 23 to 30% by volume of sunflower oil, 5 to 10% by volume of an 1:1 by volume mixture of methanol or ethanol, respectively with isobutanol in an amount supplementing up to 1 liter.

One liter of the solution of the plant protective agent according to the invention can be prepared by dissolving 1 to 150 g/l of synthetic pyrethroid, 40 to 70 g/l of ethoxylated (EO=10 to 14)-propoxylated (PO=18 to 22) nonylphenol, 10 to 20 g/l of linear calcium dodecylbenzenesulfonate, 90 to 120 g/l of polyoxyethylene(20)-sorbitan monolaurate in 500 ml of a solvent mixture (A) consisting of 9 to 11% by volume of a hydrogenated aliphatic hydrocarbon containing 45% of naphthene, 18 to 30% by volume of propylene glycol, 28 to 35% by volume of pine fatty acid, 23 to 30% by volume of sunflower oil, 5 to 10% by volume of an 1:1 by volume mixture of methanol or ethanol, transmission with isobutanol and supplementing the solution thus obtained up to 1 liter with the solvent mixture (A).

The invention further relates to a transparent emulsion of a plant protective agent having an average drop size below 100 μm;

a relative interfacial tension below 3 mN/m; and a light transmission above 95% in 0.01% concentration, above 90% in 0.1% concentration and above 85% in 1% concentration through a layer thickness of 10 mm after an examination period of 120 minutes,
which comprises 0.01 to 1.0% by volume of the above solution and water of a hardness of 0 to 500 ppm in an amount necessary to fill up to 100% by volume.

As synthetic pyrethroids, the tetramethrin [chemically 3,4,5,6-tetrahydrophthalimidomethyl (1RS)-cis-trans-chrysanthemate] and/or deltamethrin [chemically (S)-α-cyano-3-phenoxybenzyl (1R)-cis-3-(2,2-dibromvinyl)-2,2-dimethylcyclopropanecarboxylate] and/or fenpropathrin [chemically (RS)-α-cyano-3-phenoxybenzyl 2,2,3,3-tetramethylcyclopropane carboxylate] and/or fenvalerate [chemically (RS)-α-cyano-3-phenoxybenzyl (RS)-2-(4-chlorophenyl)-3-methylbutylate] and/or flucitrinate ]chemically (RS)-α-cyano-3-phenoxybenzyl (RS)-2-(4-difluoromethoxyphenyl)-3-methylbutyrate] and/or permethrin [chemically 3-phenoxybenzyl 3-(2,2-dichlorovinyl)-2,2-dimethylcyclopropane carboxylate] and/or cypermethrin [chemically (RS)-α-cyano-3-phenoxybenzyl (1RS)-cis-trans-3-(2,2-dichlorovinyl)-2,2-dimethylcyclopropane carboxylate] and/or the enantiomeric pairs of (RS)-α-cyano-3-phenoxybenzyl (1RS)-cis-trans-3-(2,2-dichlorovinyl)-2,2-dimethylcyclopropane carboxylate (1R)-cis-(S)+(1S)-cis-(R) and (1R)-trans-(S)+(1S)-trans-(R) or the mixtures thereof may be contained in the plant protective compositions according to the invention.

The stability of the diluted compositions according to the invention was studied between the concentration limits of 0.01 to 1% in the presence of salts resulting in a water hardness of 34.2 to 342 ppm by using the standardized COPAC method. Samples were taken from the emulsions after 0, 30 and 120 minutes, then after 24 hours and the drop size distribution (Zetasizer IIc) in the samples and their light transmittance at 845 μm wavelength in a 10 mm glass cuvet was examined.

The interfacial tension of the composition as related to water (CIPAC A and D) was determined by using the hanging drop method.

The composition, physico-chemical characteristics and effects of the compositions according to the invention are illustrated in detail by the following non-limiting Examples.

EXAMPLE 1

The preparations according to the compositions 1 to 16 were prepared uniformly by using the following method.

1000 ml of the solution were weighed together from the solvent mixture according to the volume ratio. 500 ml of the solution obtained were weighed into a graduated cylinder of 1000 ml volume and the synthetic pyrethroids and emulsifiers were dissolved therein. After complete dissolution, the solution was filled up to 1000 ml with the above solvent. The compositions of the preparations according to the Examples are summarized in Tables 1 and 2. The characteristics of the compositions are shown in Table 3.

The following abbreviations are used in the Tables:

| Components | Abbreviation in the Tables |
|---|---|
| Ethoxylated(EO = 13)-propoxylated(PO = 21) nonylphenol | EPN |
| Linear calcium dodecylbenzenesulfonate | LDBC |
| Polyethoxylene(20)-sorbitan monooleate | PSMO |
| Propylene glycol | PGL |
| Pine fatty acid | PFA |
| Sunflower oil | SO |
| 1:1 by volume mixture of methanol or ethanol, respectively, with isobutanol | MB or EB, respectively |
| Hydrogenated aliphatic hydrocarbon mixture containing 45% of naphthene | HAM |

TABLE 1

| Components | Compositions | | | | | | | |
|---|---|---|---|---|---|---|---|---|
| | 1 | 2 | 3 | 4 | 5 | 6 | 7 | 8 |
| Cypermethrin (g/l) | 150 | 75 | — | — | — | — | — | — |
| (1R)-cis-(S) + (1S)-cis-(R) (g/l) | — | — | 50 | — | 40 | 30 | 20 | 30 |
| (1R)-trans-(S) + (1S)-trans-(R) (g/l) | — | — | — | 50 | 60 | 70 | 30 | 20 |
| EPN (g/l) | 70 | 40 | 60 | 60 | 60 | 65 | 60 | 60 |
| LDBC (g/l) | 20 | 10 | 14 | 15 | 14 | 18 | 14 | 14 |
| PSMO (g/l) | 120 | 90 | 105 | 105 | 105 | 115 | 105 | 105 |
| completed to 1000 ml with: | | | | | | | | |
| PGL (% by vol.) | 28.6 | 19.1 | 19.1 | 19.1 | 23.8 | 23.8 | 23.8 | 23.8 |
| PFA (% by vol.) | 28.6 | 33.3 | 33.3 | 33.3 | 31.0 | 28.6 | 31.0 | 31.0 |
| SO (% by vol.) | 23.8 | 28.6 | 28.6 | 23.8 | 26.2 | 28.6 | 26.2 | 26.2 |
| EB (% by vol.) | 9.5 | 9.6 | 9.5 | 9.5 | 9.5 | 9.5 | 9.5 | 9.5 |
| HAM (% by vol.) | 9.5 | 9.5 | 9.5 | 9.5 | 9.5 | 9.5 | 9.5 | 9.5 |

TABLE 2

| Components | Compositions | | | | |
|---|---|---|---|---|---|
| | 9 | 10 | 11 | 12 | 13 |
| Deltamethrin (g/l) | 25 | — | — | — | — |
| Fenpropathrin (g/l) | — | 100 | — | — | — |
| Fenvalerate (g/l) | — | — | 110 | — | — |
| Permethrin (g/l) | — | — | — | — | 250 |
| EPN (g/l) | 60 | 60 | 60 | 60 | 70 |
| LDBC (g/l) | 14 | 14 | 18 | 14 | 20 |
| PSMO (g/l) | 105 | 105 | 115 | 105 | 12 |
| supplemented to 1000 ml with: | | | | | |
| PGL (% by vol.) | 19.1 | 23.8 | 23.8 | 19.1 | 23.8 |
| PFA (% by vol.) | 28.6 | 28.6 | 31.0 | 33.3 | 31.0 |
| SO (% by vol.) | 28.6 | 28.6 | 26.2 | 23.8 | 26.2 |
| MB (% by vol.) | 9.5 | — | — | — | 9.5 |
| EB (% by vol.) | — | 9.5 | 9.5 | 9.5 | — |
| HAM (% by vol.) | 9.5 | 9.5 | 9.5 | 9.5 | 9.5 |

| Components | 14 | 15 | 16 |
|---|---|---|---|
| (1R)-trans-(S) + (1S)-trans-(R) | 50 | 50 | 50 |
| Tetramethrin | 5 | 5 | 5 |
| Piperonylbutoxide | 100 | — | 50 |
| EPN (g/l) | 65 | 40 | 60 |
| LDBC (g/l) | 18 | 10 | 14 |
| PSMO (g/l) | 115 | 90 | 105 |
| supplemented to 1000 ml with: | | | |
| PGL (% by vol.) | 23.8 | 19.1 | 28.6 |
| TLS (% by vol.) | 31.0 | 33.3 | 28.6 |
| SO (% by vol.) | 26.2 | 28.6 | 23.8 |
| EB (% by vol.) | 9.5 | 9.5 | 9.5 |
| HAM (% by vol.) | 9.5 | 9.5 | 9.5 |

TABLE 3
Physico-chemical characteristics

| Example No. | 1 | | | 2 | | | 3 | | | 4 | | |
|---|---|---|---|---|---|---|---|---|---|---|---|---|
| Dilution (%) | 0.01 | 0.1 | 1.0 | 0.01 | 0.1 | 1.0 | 0.01 | 0.1 | 1.0 | 0.01 | 0.1 | 1.0 |
| light transmission % | | | | | | | | | | | | |
| 0 h | 98 | 94 | 90 | 99 | 95 | 87 | 95 | 92 | 85 | 97 | 93 | 82 |
| 0.5 h | 100 | 97 | 92 | 100 | 96 | 88 | 97 | 33 | 85 | 99 | 94 | 82 |
| 2 h | 100 | 98 | 92 | 100 | 96 | 88 | 97 | 94 | 87 | 100 | 94 | 84 |
| 24 h | 100 | 97 | 90 | 100 | 96 | 89 | 96 | 94 | 87 | 100 | 94 | 84 |
| Surface tension (mN/m) | | 2 | | | 0 | | | 0 | | | 3 | |
| Average drop size (nm) | | 83 | | | 57 | | | 64 | | | 87 | |

| Example No. | 5 | | | 6 | | | 7 | | | 8 | | |
|---|---|---|---|---|---|---|---|---|---|---|---|---|
| Dilution (%) | 0.01 | 0.1 | 1.0 | 0.01 | 0.1 | 1.0 | 0.01 | 0.1 | 1.0 | 0.01 | 0.1 | 1.0 |
| light transmission % | | | | | | | | | | | | |
| 0 h | 95 | 95 | 87 | 99 | 95 | 80 | 97 | 95 | 82 | 97 | 92 | 85 |
| 0.5 h | 97 | 94 | 89 | 100 | 97 | 82 | 98 | 97 | 83 | 98 | 93 | 86 |
| 2 h | 97 | 95 | 89 | 100 | 97 | 85 | 100 | 97 | 85 | 98 | 94 | 86 |
| 24 h | 96 | 94 | 87 | 100 | 97 | 85 | 100 | 97 | 83 | 98 | 94 | 86 |
| Surface tension (mN/m) | | 2 | | | 0 | | | 1 | | | 1 | |
| Average drop size (nm) | | 91 | | | 78 | | | 66 | | | 69 | |

| Example No. | 9 | | | 10 | | | 11 | | | 12 | | |
|---|---|---|---|---|---|---|---|---|---|---|---|---|
| Dilution (%) | 0.01 | 0.1 | 1.0 | 0.01 | 0.1 | 1.0 | 0.01 | 0.1 | 1.0 | 0.01 | 0.1 | 1.0 |
| light transmission % | | | | | | | | | | | | |
| 0 h | 95 | 94 | 85 | 98 | 95 | 80 | 100 | 95 | 85 | 99 | 96 | 87 |
| 0.5 h | 98 | 94 | 86 | 98 | 96 | 85 | 100 | 96 | 86 | 100 | 96 | 86 |
| 2 h | 98 | 95 | 86 | 100 | 96 | 85 | 100 | 96 | 86 | 100 | 97 | 88 |
| 24 h | 98 | 95 | 85 | 100 | 96 | 85 | 100 | 95 | 87 | 100 | 97 | 88 |
| Surface tension (mN/m) | | 0 | | | 1 | | | 1 | | | 0 | |
| Average drop size (nm) | | 93 | | | 98 | | | 76 | | | 84 | |

| Example No. | 13 | | | 14 | | | 15 | | | 16 | | |
|---|---|---|---|---|---|---|---|---|---|---|---|---|
| Dilution (%) | 0.01 | 0.1 | 1.0 | 0.01 | 0.1 | 1.0 | 0.01 | 0.1 | 1.0 | 0.01 | 0.1 | 1.0 |
| light transmission % | | | | | | | | | | | | |
| 0 h | 95 | 93 | 86 | 100 | 97 | 80 | 100 | 100 | 86 | 100 | 96 | 87 |
| 0.5 h | 97 | 94 | 87 | 100 | 97 | 84 | 99 | 96 | 87 | 100 | 94 | 84 |
| 2 h | 97 | 94 | 87 | 98 | 95 | 85 | 99 | 96 | 86 | 95 | 94 | 84 |
| 24 h | 97 | 94 | 87 | 97 | 95 | 85 | 99 | 97 | 88 | 94 | 92 | 85 |
| Surface tension (mN/m) | | 1 | | | 2 | | | 0 | | | 1 | |
| Average drop size (nm) | | 72 | | | 86 | | | 64 | | | 68 | |

EXAMPLE 17

Emulsions with a 1000-fold dilution were prepared from the samples according to the above formulation Examples by using CIPAC D water, then the activity of the emulsions was determined in a fresh state and after standing for 5 hours.

The samples taken from the upper third of the emulsions were further diluted with CIPAC D water in the given moments to obtain emulsions with concentrations of 2.5, 1.25, 0.625, 0.3125, 0.15625 and 0.078125 ppm, calculated on the active ingredient. Two ml of these emulsions were sprayed into Petri plates of 9 cm diameter by using a Potter's tower.

After complete drying, twenty 3-day old female houseflies (Musca domestica WHO/SRS with a body weight of 21±1.5 mg each) mildly narcotized by carbon dioxide were put into the Petri dishes and after 24 hours the number of the dead flies was determined. This examination was carried out for each concentration in 3 parallels.

From the data obtained the equipotential concentrations ($LC_{50}$ values) expressing the activity were calculated by probit analysis. The lower $LC_{50}$ values mean higher activities. The results are summarized in Table 4.

TABLE 4

| Samples | Duration of the activity examination after preparation of the emulsion (hour) | $LC_{50}\pm$ | s | b |
|---|---|---|---|---|
| CNX 5 EC Example, control | 0 | 0.564 | 0.047 | 2.26 |
| CHX 5 ME Example 7, product | 0 | 0.263 | 0.021 | 2.43 |
| CHX 5 EC Example, control | 5 | 0.594 | 0.052 | 2.131 |

| Composition of CHX 5 EC: | |
|---|---|
| (1R)-cis-(S) + (1S)-cis-(R) (g/l) | 20 |
| (1R)-trans-(S) + (1S)-trans-(R) (g/l) | 30 |
| Emulsifiers (g/l) | 100 |
| Xylene completed to | 1000 ml |

EXAMPLES 18 to 27

The aerosols shown in Table 5 are prepared from the aqueous microemulsions according to the invention in a manner known per se.

TABLE 5

| | Example No. | | | | | | | | | |
|---|---|---|---|---|---|---|---|---|---|---|
| | 18 | 19 | 20 | 21 | 22 | 23 | 24 | 25 | 26 | 27 |
| Composition of Example 4 in an aqueous dilution of 1% (% by vol.) | 40 | 40 | — | — | — | — | — | — | — | — |
| Composition of Example 7 in an aqueous dilution of 1% (% by vol.) | — | — | 40 | 40 | — | — | — | — | — | — |
| Composition of Example 14 in an aquoue dilution of 1% (% by vol.) | — | — | — | — | 40 | 40 | — | — | — | — |
| Composition of Example 15 in an aqueous dilution of 1% (% by vol.) | — | — | — | — | — | — | 40 | 40 | — | — |
| Composition of Example 16 in an aqueous dilution of 1% (% by vol.) | — | — | — | — | — | — | — | — | 40 | 40 |
| Ethanol (% by vol.) | 20 | — | 20 | — | 20 | — | 20 | — | 20 | — |
| Liquid propane-butane (% by vol.) | 40 | 40 | 40 | 40 | 40 | 40 | 40 | 40 | 40 | 40 |
| Isopropanol (% by vol.) | — | 20 | — | 20 | — | 20 | — | 20 | — | 20 |

What is claimed is:

1. A solution of a plant protective agent which comprises
    as active ingredient 1–150 g of at least one synthetic pyrethroid
    as a surface active agent 40–70 g of ethoxylated (EO = 10–14)-propoxylated (PO = 18–22) nonylphenol,
    10–20 g of linear calcium dodecylbenzene sulfonate, and
    90–120 g of polyoxyethylene (20)-sorbitan monolaurate, and a solvent mixture in a quantity needed for 1 liter from the following (A) composition:
    9–11% by volume of a hydrogenated aliphatic hydrocarbon containing 45% of naphthene,
    18–30% by volume of propylene glycol,
    28–35% by volume of pine fatty acid,
    25–30% by volume of sunflower oil, and
    5–10% by volume of a 1:1 by volume mixture of methanol or ethanol with isobutanol.

2. Process for the preparation of a plant protective agent solution according to claim 1, which comprises dissolving
    1–150 g of a synthetic pyrethroid,
    40–70 g of ethoxylated (EO = 10–14)-propoxylated (PO = 18–22) nonylphenol,
    10–20 g of linear calcium dodecylbenzene sulfonate,
    90–120 g of polyoxyethylene (20)-sorbitan monolaurate in 500 ml of a solvent mixture of the following composition (A):
    9–11% by volume of a hydrogenated aliphatic hydrocarbon containing 45% of naphthene,
    18–35% by volume of propylene glycol,
    28–35% by volume of pine fatty acid,
    28–30% by volume of sunflower oil,
    5–10% by volume of an 1:1 by volume mixture of methanol or
    ethanol and isobutanol,
    and the solution thus obtained is completed to 1 liter by the solution mixture (A).

3. Transparent plant protective agent emulsion having an average drop size below 100 μm;
    a relative interfacial tension below 3 mH/m, and
    a light transmission capacity at a layer thickness of 10 mm after an examination period of 120 minutes in a concentration after an examination period of 120 minutes in a concentration of
    0.01% T above 95%
    0.1% T above 90% and
    1% T above 80%,
    which contains 0.01 to 1.0% by volume of the solution according to claim 1 and water of a hardness of 0–500 ppm of the sum of all milliequivalents of cations contributing to hardness, calculated as $CaCO_3$.

4. Plant protective compositions according to claim 1, which comprise synthetic pyrethroids 3,4,5,6-tetrahydro-phthalimidomethyl (1RS)-cis-trans-chrysanthemate;
    (S)-α-cyano-3-phenoxybenzyl (1R)-cis-3-(2,2-dibromovinyl)-2,2-dimethyl-cyclopropane carboxylate;
    (RS)-α-cyano-3-phenoxybenzyl-(RS)-2-(4-chlorophenyl)-3-methylbutyrate;
    3-phenoxybenzyl-3-(2,2-dichlorovinyl)-2,2-dimethylcyclopropane carboxylate;
    (RS)-α-cyano-3-phenoxybenzyl-(1RS)-cis-trans-3-(2,2-dichlorovinyl)-2,2-dimethylcyclopropane carboxylate; or the enantiomeric pairs of (RS)-α-cyano-3-phenoxybenzyl (1RS)-cis-trans-3-3(2,2-dichlorovinyl)-2,2-dimethylcyclopropane carboxylate (1R)-cis-(S)÷(1S)-cis-(R) and (1R)-trans-(S)÷(1S)-trans-(R); or mixtures thereof.

5. A solution of a plant protective agent which comprises,
    (a) as active ingredients:
        (1) 20 g of the cypermethrin isomer pair 1RcisS and 1ScisR; and
        (2) 30 g of the cypermethrin isomer pair 1RtransS and 1StransR;
    (b) as a surface active agent:
        (1) 60 g of ethoxylated(EO = 13)-propoxylated(PO = 21) nonylphenol;
        (2) 14 g of linear calcium dodecyl benzene sulfonate; and
        (3) 105 g of polyoxyethylene(20)-sorbitan monooleate; and
    (c) as a solvent mixture in a quantity needed for 1 liter from the following composition:
        (1) 23.8% by volume of propylene glycol;
        (2) 31.0% by volume of pine fatty acid;
        (3) 26.2% by volume of sunflower oil;
        (4) 9.5% by volume of a 1:1 parts by volume mixture of ethanol and isobutanol; and
        (5) 9.5% by volume of a hydrogenated aliphatic hydrocarbon mixture comprising 45% of naphthene.

* * * * *